(12) United States Patent
Hutcherson et al.

(10) Patent No.: US 6,727,230 B1
(45) Date of Patent: *Apr. 27, 2004

(54) IMMUNE STIMULATION BY PHOSPHOROTHIOATE OLIGONUCLEOTIDE ANALOGS

(75) Inventors: Stephen L. Hutcherson, Richmond, VA (US); Josephine M. Glover, Woking (GB)

(73) Assignee: Coley Pharmaceutical Group, Inc., Wellesley, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/009,634

(22) Filed: Jan. 20, 1998

Related U.S. Application Data

(63) Continuation of application No. 08/712,135, filed on Sep. 11, 1996, now Pat. No. 5,723,335, which is a continuation of application No. 08/217,988, filed on Mar. 25, 1994, now abandoned.

(51) Int. Cl.[7] .......................... A61K 31/00; C07H 21/04
(52) U.S. Cl. ..................... 514/44; 536/23.1; 536/24.31; 536/24.33; 536/24.5; 435/6; 435/91.1; 435/325; 435/366; 435/375
(58) Field of Search ..................... 435/6, 91.1, 91.31, 435/325, 366, 375; 536/23.1, 24.3, 24.5; 514/44

(56) References Cited

U.S. PATENT DOCUMENTS

| | | | |
|---|---|---|---|
| 3,906,092 A | | 9/1975 | Hilleman et al. |
| 4,469,863 A | | 9/1984 | Ts'o et al. |
| 4,956,296 A | | 9/1990 | Fahnestock |
| 5,023,243 A | | 6/1991 | Tullis |
| 5,234,811 A | | 8/1993 | Beutler et al. |
| 5,248,670 A | | 9/1993 | Draper et al. |
| 5,457,189 A | | 10/1995 | Crooke et al. |
| 5,491,088 A | | 2/1996 | Hellstrom et al. |
| 5,506,212 A | | 4/1996 | Hoke et al. |
| 5,514,577 A | | 5/1996 | Draper |
| 5,565,203 A | | 10/1996 | Glück et al. |
| 5,576,208 A | | 11/1996 | Monia et al. |
| 5,582,986 A | | 12/1996 | Monia et al. |
| 5,585,479 A | | 12/1996 | Hoke et al. |
| 5,589,466 A | | 12/1996 | Felgner et al. |
| 5,591,721 A | | 1/1997 | Agrawal et al. |
| 5,599,797 A | | 2/1997 | Cook et al. |
| 5,663,153 A | * | 9/1997 | Hutcherson et al. .......... 514/44 |
| 5,679,647 A | | 10/1997 | Carson et al. |
| 5,723,130 A | | 3/1998 | Hancock et al. |
| 5,723,335 A | * | 3/1998 | Hutcherson et al. ........ 435/375 |
| 5,736,524 A | | 4/1998 | Content et al. |
| 5,756,097 A | | 5/1998 | Landucci et al. |
| 5,780,448 A | | 7/1998 | Davis |
| 5,786,189 A | | 7/1998 | Locht et al. |
| 5,804,566 A | | 9/1998 | Carson et al. |
| 5,837,243 A | | 11/1998 | Deo et al. |
| 5,849,719 A | | 12/1998 | Carson |
| 5,976,567 A | | 11/1999 | Wheeler et al. |
| 6,030,955 A | | 2/2000 | Stein et al. |
| 6,194,388 B1 | | 2/2001 | Krieg et al. |
| 6,207,646 B1 | | 3/2001 | Krieg et al. |
| 6,214,806 B1 | | 4/2001 | Krieg et al. |
| 6,218,371 B1 | | 4/2001 | Krieg et al. |
| 6,239,116 B1 | | 5/2001 | Krieg et al. |
| 6,339,068 B1 | | 1/2002 | Krieg et al. |
| 6,406,705 B1 | | 6/2002 | Davis et al. |
| 6,429,199 B1 | | 8/2002 | Krieg et al. |

FOREIGN PATENT DOCUMENTS

| | | |
|---|---|---|
| EP | 0 092 574 | 11/1983 |
| EP | 0 468 520 | 1/1992 |
| EP | 0 302 758 | 3/1994 |
| WO | WO 91/12811 | 9/1991 |
| WO | WO 92/03456 | 3/1992 |
| WO | WO 92/18522 | 10/1992 |
| WO | WO 92/21353 | 12/1992 |
| WO | WO 94/19945 | 9/1994 |
| WO | WO 95/05853 | 3/1995 |
| WO | WO 95/26204 | 10/1995 |
| WO | WO 96/02555 | 2/1996 |
| WO | WO 96/35782 | 11/1996 |
| WO | WO 97/28259 | 8/1997 |
| WO | WO 98/14210 | 4/1998 |
| WO | WO 98/16247 A1 | 4/1998 |
| WO | WO 98/18810 | 5/1998 |
| WO | WO 98/32462 A1 | 7/1998 |
| WO | WO 98/37919 | 9/1998 |

(List continued on next page.)

OTHER PUBLICATIONS

Branch, TIBS 23 pp. 45–50, Feb. 1998.*
Flanagan et al., Nature Biotech. 17:48–52, Jan. 1999.*
Weiner et al., PNAS 94:10833–10837, Sep. 1997.*

(List continued on next page.)

*Primary Examiner*—John L. LeGuyader
*Assistant Examiner*—M Schmidt
(74) *Attorney, Agent, or Firm*—Wolf, Greenfield & Sacks, P.C.

(57) ABSTRACT

Methods of stimulating a local immune response in selected cells or tissues employing immunopotentiating oligonucleotide analogs having at least one phosphorothioate internucleotide bond are provided. Methods of enhancing the efficacy of a therapeutic treatment by stimulating a local immune response in selected cells or tissues employing oligonucleotide analogs having at least one phosphorothioate bond are also provided. The oligonucleotide analogs may have antisense efficacy in addition to immunopotentiating activity. Methods of modulating cytokine release in skin cells and immunopotentiators which include oligonucleotide analogs having at least one phosphorothioate bond capable of eliciting a local inflammatory response are also provided.

14 Claims, No Drawings

FOREIGN PATENT DOCUMENTS

| WO | WO 98/40100 | | 9/1998 |
|---|---|---|---|
| WO | WO 98/55495 | A2 | 12/1998 |
| WO | WO 98/55609 | A1 | 12/1998 |
| WO | WO 99/55743 | A1 | 11/1999 |
| WO | WO 01/02007 | A1 | 1/2001 |
| WO | WO 01/12223 | A2 | 2/2001 |

OTHER PUBLICATIONS

Allison et al., Mol. Immunology 28(3):279–284, 1991.*

Mojcik et al., Clinical Imm & Immunopathology, 67(2):130–136, 1993.*

Agrawal, S. et al., "Pharmacokinetics of Antisense Oligonucleotides", Clin. Pharmacokinet., 1995, pp. 7–16, vol. 28, No. 1.

Agrawal, S., "Antisense oligonucleotides: towards clinical trials", TIBTECH, Oct. 1996, pp. 376–387, vol. 14, Elsevier Trends Journals.

Agrawal, S. et al., "Toxicologic Effects of an Oligodeoxynucleotide Phosphorothioate and Its Analogs Following Intravenous Administration in Rats", Antisense & Nucleic Acid Drug Development, 1997, pp. 575–584, vol. 7, Mary Ann Liebert, Inc.

Benimetskaya, L. et al., "Formation of a G–tetrad and higher order structures correlates with biological activity of the RelA (NF–κB p65) 'antisense' oligodeoxynucleotide", Nucleic Acids Research, 1997, pp. 2648–2656, vol. 25, No. 13, Oxford University Press.

Burgess, T.L. et al., "The antiproliferative activity of c–myb antisense oligonucleotides in smooth muscle cells is caused by a nonantisense mechanism", Proc. Natl. Acad. Sci. USA, Apr. 1995, pp. 4051–4055, vol. 92.

Hertl, M. et al., "Inhibition of Interferon–γ–Induced Intercellular Adhesion Molecule–1 Expression on Human Keratinocytes by Phosphorothioate Antisense Oligodeoxynucleotides is the Consequence of Antisense–Specific and Antisense–Non–Specific Effects", The Journal of Investigative Dermatology, May 1995, pp. 813–817, vol. 104, No. 5, The Society for Investigative Dermatology, Inc.

Lacour, J., "Clinical Trials Using Polyadenylic–Polyuridylic Acid as an Adjuvant to Surgery in Treating Different Human Tumors", Journal of Biological Response Modifiers, 1985, pp. 538–543, vol. 4, Raven Press, New York.

Lederman, S. et al., "Polydeoxyguanine Motifs in a 12–mer Phosphorothioate Oligodeoxynucleotide Augment Binding of the v3 Loop of HIV–1 gp120 and Potency of HIV–1 Inhibition Independently of G–Trend Formation", Antisense & Nucleic Acid Drug Development, 1996, pp. 281–289, vol. 6, Mary Ann Liebert, Inc.

Maltese, J.Y. et al., "Sequence context of antisense RelA/NF–κB phosphorothioates determines specificity", Nucleic Acids Research, 1995, pp. 1146–1151, vol. 23, No. 7, Oxford University Press.

Sands, H. et al., "Biodistribution and Metabolism of Internally $^3$H–Labeled Oligonucleotides. I. Comparison of a Phosphodiester and a Phosphorothioate", Molecular Pharmacology, 1994, pp. 932–943, vol. 45, The American Society for Pharmacology and Experimental Therapeutics.

Cossum, et al. "Pharmacokinetics of a $^{14}$C–labeled phosphorothioate oligonucleotide, ISIS 2105, after Intradermal administration of rats", J. of Pharm. and Exper. Therapeutics, 269(1):89–94 (1994).

Krieg, et al., "A role for endogenous retroviral sequences in the regulation of lymphocyte activation", J. of Immunol., 143(8):2448–2451 (1989).

McIntyre, et al., "A sense phosphorothioate oligonucleotide directed to the initiation codon of transcription factor NF–KB p65 causes sequence–specific immune stimulation", Antisense Res. and Develp., 3:309–322 (1993).

Yaswen, et al., "Effects of sequence of thioated oligonucleotides on cultured human mammary epithelial cells", Antisense Res. and Develp., 3:67–77 (1993).

Branda, R.F. et al., Immune Stimulation by an Antisense Oligomer Complementary to the rev Gene of HIV–1, Biochemical Pharmacology, 1993, 45, 2037–2043.

Gerwirtz, A.M. et al., $G_1$/S Transition in Normal Human T–Lymphocytes Requires the Nuclear Protein Encoded by c–myb, Scinece 1989, 245, 180–183.

Jachimczak, P. et al., The effect of transforming growth factor–$\beta_2$–specific phosphorothioate–anti–sense oligodeoxynucleotides in reversing cellular immunosuppression in malignant glioma, J. Neurosurg, 1993, 78, 944–951.

Kloc, M. et al., Interleukin–2 Antisense Oligonucleotides Inhibit in vitro Functions of T Cells, Faseb J., 1991, 5, A973.

Krieg, A.M. et al., A Role for Endogenous Retroviral Sequences in the Regulation of Lymphocyte Activation, J. Immun., 1989, 143, 2448–2451.

Kuramoto, E. et al., Oligonucleotide Sequences Required for Natural Killer Cell Activation, Jpn. J. Cancer Res., 1992, 83, 1128–1131.

McIntyre, K.W. et al., A Sense Phosphorothioate Oligonucleotide Directed to the Initiation Codon of Transcription Factor NF–κK p65 Causes Sequence–Specific Immune Stimulation, Antisense Research and Development, 1993, 3, 309–322.

Pisetsky, D.S. et al., Stimulation of Murine Lymphocyte Proliferation by a Phosphorothioate Oligonucleotide with Antisense Activity for Herpes Simplex Virus, Life Sciences, 1994, 54, 101–107.

Rodgers, K.E., et al., Toxicology, 1988, 51, 241–253.

Rodgers, K.E., et al., Investigations into the Mechanism of Immunosuppression Caused by Acute Treatment with O,O, S–Trimethyl Phosphorothioate: Generation of Suppression Macrophages from Treated Animals, Toxicology and Applied Pharmacology, 1987, 88, 270–281.

Abken, et al., "Four cell–secreted cytokines act synergistically to maintain long term proliferation of human B cell lines in vitro", J. of Immunol., 149(8):2785–2795 (1992).

Adya, et al., "Expression of CREB's DNA recognition specificity by Tax results from interaction iwht Ala–Ala–Arg at positions 282–284 near the conserved DNA–binding domain of CREB", Proc. Natl. Acad. Sci., USA 91(12):5642–6, (1994).

Aggarwal, et al., "Cell–surface–associated nucleic acid tumorigenic cells made visible with platinum–pyrimidine complexes by electron microscopy", Proc. Natl. Acad. Sci. USA 72(3):928–32, Mar., 1995.

Anfossi, et al., PNAS, 86(9):3379–93 (1989).

Angier, "Microbe DNA seen as alien by immune cells", N. New York Times Apr. 11, 1995.

Arany, et al., Cell, 77(6):799–800 (1994).

Arias, et al., "Activation of cAMP and mitogen responsive genes relies on a common nuclear factor", Nature 370:226–9 (1994).

Asiedu, et al., "Binding of AP–1/CREB proteins and of MDBP to contiguous sites downstream of the human TGF–β1 gene", *Biochim Biophys. Acta.*, 1219(1):55–63 (1994).

Azad, et al., "Antiviral activity of phosphorothioate oligonucleotide complementary of RNA of the human cytomegalovirus major immediate–early region", *Antimicrobial Agents and Chemotherapy*, 37:1945–1954, (1993).

Azuma, et al., "Immunological properties of muramyldipeptides (MDP) and related synthetic compounds", *Kekkaku*, 67(9):625–631, (45–55) 1992.

Ballas, et al., "NK1.1+ Thymocytes: Adult murine CD4–, CD8–thymocytes contain an NK1.1$^{30}$, CD3$^{30}$, CD5$^{hi}$, CD44$^{hi}$, TCR–Vβ8$^{30}$ subset", *J. Immunol.*, 145(4):1039–45, 1990.

Ballas, et al., "Introduction of NK activity in murine and human cells by CpG motifs in oligodeoxynucleotides and bacterial DNA", *J Immunol* 157(5):1840–5, 1996.

Ballas, et al., "Lympholine–activated killer cells", *J. Immunol.*, 150(1):17–30, 1993.

Bayever, E., "Systemic administration of a phosphorothioate oligonucleotide with a sequence complementary to p53 for acute myelogenous leukemia and myelodysplastic syndrome: initial results of a phase I trial", *Antisense Res. & Dev.* (1993), 3:383–390.

Beaucage, et al., *Tetrahedron Lett.*, 22(20):1859–62, 1981.

Bennett, et al, "DNA binding to human leukocytes", *J Clin Invest* 76(6):2182–90, 1985.

Berg, et al., "DNA binding to human leukocytes", *J Clin Invest* 96(5):2339–47, 1995.

Bickel, et al., *J. Dental. Res.*, 75(11):1827–34, Biosis Abstract, 1996.

Blanchard, et al., "Interferon–γ Induction by lipopolysaccharide: dependence on interleukin 2 and macrophages", *J Immunol* 136(3):963–70, 1986.

Blaxter et al., "Genes expressed in *Brugia malayi* infective third stage larvae", *Mol. and Biochem. Parasitology*, 77:77–93, Apr. 1999.

Boggs, et al., "Characterization and modulation of immune stimulation by modified oligonucleotides", *Antisense Nucleic Acid Drug Dev* 7(5):461–71, Oct. 1997.

Branda, et al., "Amplification of antibody production by phosphorothioate oligodeoxynucleotides", *J. Lab Clin Med* 128(3):329–38, 1996.

Briskin, et al., "Lipopolysaccharide–unresponsive mutant pre–B–cell lines blocked in NF–κB activation", *Mol Cell Biol* 10(1):422–5, 1990.

Chace, et al., "Regulation of differentiation in CD5$^+$ and conventional B cells", *Clinical Immunology and Immunopathology*, (1993), 68(3):327–332.

Chang, et al., "The palindromic series I repeats in the simian cytomegalovirus major immediate–early promoter behave as both strong basal enhancers and cyclic AMP response elements", *J Virol* 64(1):264–77, 1990.

Chu, et al., "CpG oligodeoxynucleotides act as adjuvants that switch on T helper 1 (Th1) Immunity", *J Exp Med* 186(10):1623–31, 17 1997.

Coggswell, et al., "NK–κB regulates IL–1β transcription through a consensus NF–κB binding site and a nonconsensus CFR–like site", *J Immunol.*, 153(2):712–23, 1994.

Constant, et al., "Stimulation of human γδ T cells by nonpeptidic mycobacterial ligands", *Science*, 264:267–70, 1994.

Cowdery, et al., "Bacterial DNA induces NK cells to produce IFN–γ in vivo and increases the toxicity of lipopolysaccarides", *J Immunol* 156(12):4570–5, 15 1996.

Cowsert, et al., "In vitro evaluation of phosphorothioate oligonucleotides targeted to the E2 mRNA of papillomavirus: potential treatment of genital warts", *Antimicrobial Agents and Chemotherapy*, 171–177 (1993).

Cox, et al., "A ATF/CREB binding motif is required for aberrant constitutive expression of the MHC class II DRα promoter and activation by SV40 T–antigen", *Nucleic Acids Res.*, 20(18):4881–7, 1992.

Crooke, et al., *Toxical. & Appln. Pharmacol.*, 140(1):85–93 Biosis Abstract, 1996.

Crosby, et al., "The early response gene NGFI–C encodes a zinc finger transcriptional activator and is a member of the GCGGGGGcG (GSG) element–binding protein family", *Mol. Cell. Biol.*, 11(8):3835–41, 1991.

Crystal R., "Transfer of genes to humans: Early lessons and obstacles to success" *Science*, vol. 270, pp. 404–410, 1995.

D'Andrea, et al., "Interleukin 10 (IL–10) inhibits human lymphocyte interferon γ–production by suppressing natural killer cell stimulatory factor/IL–2 synthesis in accessory cells", *J Exp Med* 178(3):1041–8, 1993.

de Groot, et al., "Hormone control of gene expression: multiplicity and versatility of cyclic adenosine 3',5'–monophosphate–responsive nuclear regulators", *Mol. Endocrinol.*, 7(2):145–53, 1993.

Du, et al., "An ATF/CREB binding site protein is required for virus induction of the human interferon β gene", *Proc. Natl. Acad. Sci. USA*, 89(6):2150–4, 1992.

Du, et al., "Mechanisms of transcriptional synergism between distinct virus–inducible enhancer elements", *Cell*, 74(5):887–98, 1993.

Englisch et al., "Chemically modified oligonucleotides as probes and inhibitors", *Angew. Chem. Int. Ed. Engl.*, 30:613–629, 1991.

Erb, et al., "Infection of mice with mycobacterium bovis–Bacillus Calmette–Guerin (BCG) suppresses allergen–induced airway eosinophilia", *J Exp Med* 187(4):561–9, Feb. 16, 1998.

Eskelinen, et al., "Optimum treatment of genital warts", *Drugs* 34(5):599–603 (1987).

Etlinger, "Carrier sequence selection—one key to successful vaccines", *Immunology Today*, 13(2):52–55, 1992.

Ewel, et al., "Polyinosinic–polycytidylic acid complexed with poly–L–lysine and carboxymethylcellulose in combination with interleukin–2 in patients with cancer: Clinical and immunological effects", *Cancer Res.*, 52(11):3005–10, 1992.

Feldbush, et al., "Lymphokine–like activity of 8–mercaptoguanosine: Induction of T and B cell differentiation", *J. Immunol.*, 134(5):3204–11, 1985.

Ferrari, et al., "The cAmp–regulated transcription factor CREB interacts with a component of the TFIID complex", *Proc. Natl. Acad. Sci. USA*, 91(4):1210–3, 1994.

Fox RI, "Mechanism of Action of hydroxychloroquine as an antiheumatic drug", *Seminars in Arthritis and Rheumatism* 23(2 Supp 1):82–91 (1993) (same as) *Chem. Abstracts* 120(15):182630 (1994).

Gaffney, et al., "Large–scale oligonucleotide synthesis by the H–phosphonate method", *Tetrahedron Letters* 29(22):2619–22, 1988.

Gao, et al., "Phosphorothioate oligonucleotides are inhibitors of human DNA polymerase and Rnase H: impliations for antisense technology", *Mol Pharmacol.* 41(2):223–229 (1992).

Garegg, et al., "Nucleoside H–phosphonatees. III. Chemical synthesis of oligodeoxyribonucleotides by the hydrogen-phosphonate approach", *Tetrahedron Letters* 27(34):4051–54, 1986.

Garegg, et al., "Nucleoside H–phosphonates. IV. Automated solid phase synthesis of oligoribonucleotides by the hydrogenphosphonate approach", *Tetrahedron Letters* 27(34):4055–58, 1986.

Goodchild, J., "Conjugates of oligonucleotides and modified oligonucleotides: A review of their synthesis and properties", *Bioconjug Chem.*, 1(3):165–87, 1990.

Goodman, MG, "Mechanism of synergy between T cell signals and C8–substituted guanine nucleosides in humoral immunity: B lymphotropic cytokines induce responsiveness to 8–mercaptuguanosine", *J. Immunol.*, 136(9):3335–40. 1986.

Gray, et al., "Antisense DNA inhibition of tumor growth induced by c–Ha–ras oncogene in nude mice", *Cancer Res.* 53(3):577–80, 1993.

Gura, T., *Science* (1995), 270:575–576.

Hadden J et al., "Immunomodulation", *TIPS*, (1993), 141:169–174.

Hadden J et al., "Immunopharmacology: Immunomodulation and Immunotherapy", *JAMA*, (1992) 268:20:2964–2969.

Halpern MD et al., "Bacterial DNA induces murine interferon–γ production by stimulation of interleukin–12 and tumor necrosis factor–α", *Cell Immunol* 167(1):72–8, 1996.

Hatzfeld J., "Release of early human hematopoietic progenitors from quiescence by antisense transforming growth factor β1 or Rb oligonucleotides", *J. Exp. Med.*, (1991) 174:925–929.

Highfield PE, "Sepsis: The more, the murkier", *Biotechnology*, 12:828, (1994).

Himes, et al., "HTLV–1 tax activation of the GM–CSF and G–CSF promoters requires the interaction of NK–γB with other transciption factor families", *Oncogene* 8(12):3189–97, 1993.

Hoeffler, et al., "Identification of multiple nuclear factors that interact with cyclic adenosine 3',5'–monophosphate response element–binding protein and activating transcription factor–2 by protein–protein interactions", *Mol Endocrinol* 5(2):256–66, 1991.

Huang, et al., "Promoter activity of the proliferating–cell nuclear antigen gene is associated with inducible CRE–binding proteins in interleukin 2–stimulated T lymphocytes", *Mol. Cell. Biol.*, 14(6):4233–43, 1994.

Hunter, et al., "Hypergammaglobulinemia and erythrocyte autoantibody complicate enzyme immunoassay of antimalarial antibody", *J. Immunoassay* 2(2):99–108, 1981.

Iguchi–Ariga SM and Shaffner W, "CpG methylation of the cAMP–responsive enhancer/promoter sequence TGACGTCA abolishes specific factor binding as well as transcriptional activation", *Genes Dev* 3(5):612–9, 1989.

Ishikawa, et al., "IFN induction and associated changes in splenic leukocyte distribution", *J Immunol* 150(9):3713–27, 1993.

Iverson, et al., *Anti–Cancer Drug Design* 6;531–8, 1991.

Iverson et al., *Antisense Research and Development*, "Pharmacokinetics of an antisense phosphorothioate oligodeoxynucleotide against rev from human immunodeficiency virus type I in the adult mail rat followintg single injections and continuous infusion", 4:43–52 (1994).

Jakway, et al., "Growth regulation of the B lymphoma cell line WEHI–231 by anti–immunoglobulin, lipopolysaccharide, and other bacterial products", *J Immunol* 137(7):2225–31, 1986.

James, et al., "The influence of adjuvant on induction of protective immunity by a non–living vaccine against schistosomiasis", *J Immunol.*, 140(8):2753–9 (1988).

Jaroszewski JW and Cohen JS, "Cellular update of antisense oligodeoxynucleotides", *Adv Drug Delivery Rev* 6(3):235–50, 1991.

Kataoka, et al., "Antitumor activity of synthetic oligonucleotides with sequences from cDNA encoding proteins of *Mycobacterium bovis* BCG", *Jpn. J. Cancer Res.*, 83:244–247 (1992).

Kimura Y et al., "Binding of oligoguanylate to scavenger receptors is required for oligonucleotides to augment NK cell activity oand induces IFN", *J. Biochem.*, 116(5):991–994, 1994.

Kline, et al., "CpG motif oligonucleotides are effective imprevention of eosinophilic inflammation in a murine model of asthma", *J Invest Med* 44(7):380A, 1996 Abstract.

Kline, et al., "Immune redirection by CpG oligonucleotides: Conversion of a Th2 response to a Th1 response in a murine model of asthma", *J Invest Med* 45(3):282A, 1997 Abstract.

Kline, et al., "CpG oligonucleotides can reverse as well as prevent Th2–mediated inflammation in a murine model of asthma" *J Invest Med* 45(7):298A, 1997 Abstract.

Klinman, et al., "Development of the autoimmune B cell repertoire in MRL–lpr/lpr mice", *Immunol.*, 144(2):506–11, 1990.

Klinman, et al., "CpG motifs present in bacterial DNA rapidly induce lymphocytes to secrete interleukin 6, interleukin 12, and interferonγ", *Proc Natl Acad Sci USA* 93(7):2879–83, 1996.

Koo, et al., "Activation of murine natural killer cells and macrophages by 8–bromoguanosine", *J. Immunol.* 140(9):3249–52, 1988.

Krajewski, et al., "A monomeric derivative of the cellular transcription factor CREB functions as a constitutive activator", *Mol. Cell. Biol.*, 14(11):7204–10, 1994.

Krieg AM et al., "Uptake of oligodeoxyribonucleotides by lymphoid cells is heterogeneous and inducible", *Antisense Res Dev* 1(2):161–71, Summer 1991.

Krieg AM et al., "Oligodeoxynucleotide modifications determine the magnitude of B cell stimulation by CpG motifs", *Antisense Nucleic Acid Drug Dev* 6(2):133–9, Summer 1996.

Krieg AM et al., "Modification of antisense phosphodiester oligodeoxynucleotides by a 5' cholesteryl moiety increases cellular association and improves efficacy", *Proc. Natl. Acad. Sci.*, (1993), 90:1048–1052.

Krieg AM et al., "CpG DNA: A pathogenic factor in systemic lupus erythematosus?", *J. Clin. Immunol.*, 15(6):284–292, 1995.

Krieg AM et al., "Phosphorothioate oligodeoxynucleotides: antisense or anti–protein?", *Antisense Res. Dev.*, 5:241, 1995.

Krieg AM et al., "Leukocyte stimulation by oligodeoxynucleotides", *Applied Antisense Oligonucleotide Technology*, 431–448, 1998.

Krieg AM et al., "The role of CpG dinucleotides in DNA vaccines", *Trends in Microbiology*, 6:23–27, 1998.

Krieg AM, "An innate immune defense mechanism based on the recognition of CpG motifs in microbial DNA", *J Lab Clin Med* 128(2);128–33, 1996.

Krieg, et al., "CpG motifs in bacterial DNA trigger direct B–cell activation", *Nature* 374:546–549 (1995).

Krown, et al., "Interleukin 1 binds to specific receptors on human keratinocytes and induces granulocytes macrophage colony–stimulating factor mRNA and protein", *J. Clin. Invest.*, 82:1787–1792 (1988).

Kupper, et al., "Interleukin 1 binds to specific receptors on human keratinocytes and induces granulocytes macrophage colony–stimulating factor mRNA and protein", *J. Clin. Invest.*, 82:1787–1792 (1988).

Kwok, et al., "Nuclear protein CBP is a coactivator for the transcription factor CREB", *Nature*, 370:223–6, 1994.

Lagrange, et al., "Immune responses directed against infectious and parasitic agents", *The Principal Types of Immune Responses*, 464–502.

Lee, et al., "Transcriptional regulation by CREB and its relatives", *Biochim Biophys Acta*, 1174(3):221–33, 1993.

Leibson, et al., "B cell helper factors: I. Requirement for both interleukin 2 nad another 40,000 mol wt factor",*J. Exp. Med.*, 154(5):1681–93, 1981.

Leonard et al., "Conformation of guanine–Boxadenine base pairs in the crystal structure of d(CGCGAATT(O8A)GCG)", *Biochemistry*, 31(36):8415–8420, 1992.

Lerner, et al., "Membrane–associated DNA in the cytoplasm of diploid human lymphocytes",*Proc. Natl. Acad. Sci.* USA, 68(6):1212–6, 1971.

Liang, et al., "Activation of human B cells by phosphorothioate oligodeoxynucleotides", *J. Clin. Invest.*, 98:1119–1129 (1996).

Liu, et al., "Promoter targeting by adenovirus E1a through interaction with different cellular DNA–binding domains", *Nature*, 368:520–5, 1994.

Loke, et al., "Delivery of c–myc Antisense phosphorothioate oligodeoxynucleotides to hematopoietic cells in culture by liposome fusion:specific reduction in c–myc protein expression correlates with inhibition of cell growth and DNA synthesis", *Current Topics in Mirobiology and Immunology*, 141:282–289 (1988).

Macfarlene DE and Manzel L, "Antagonism of immunostimulatory CpG–oligodeoxynucleotides by quinacrine, chloroquine, and structurally related compounds",*J Immunol* 160(3):1122–31, 1998.

Manzel L and Macfarlane DE, "Lack of immune stimulation by immobilized CpG–oligodeoxynucleotide", *Antisense & Nucleic Acid Drug Development*, 459–464, 1999.

Mastrangelo, et al., "Gene therapy for human cancer: an essay for clinicians", *Seminars in Oncology.* 23(1):4–21, Feb. 1996.

Matson S and Krieg AM, "Nonspecific suppression of [$^3$H]thymidine incorporated by "confront" oligonucleotides", *Antisense Res Dev* 2(4):325–30, Winter 1992.

Matsukura, et al., "Regulation of viral expression of human immunodeficiency virus in vitro by an antisense phosphorothioate oligodeoxynucleotide against rev (art/trs) in chronically infected cells", *Proc. Natl. Acad. Sci* USA, 86:4244–4248 (1989).

Messina et al., "The influence of DNA structure on the in vitro stimulation of murine lymphocytes by natural and synthetic polynucleotide antigens", *Cellular Immunology*, 147(1):148–157, 1993.

Messina et al., "Stimulation of in vitro murine lymphocyte proliferation of bacterial DNA", *J. Immunol.*, 147(6):1759–1764, (1991).

Monia, et al., "Selective inhibition of mutant Ha–ras mRNA expression by antisense oligonucleotides", *J. Biol. Chem.*, 267(28):19954–19962 (1992).

Mottram et al., "A novel CDC2–related protein kinase from *Leishmania mexicana*, LmmCRK1, is post–transitionally regulated during the life cycle", *J. Biol. Chem.* 268:28, 21044–21052 (Oct. 1993).

New England Biolabs 1988–1989 Catalog.

Nyce and Metzger, "DNA antisense therapy for asthma in an animal model", *Nature* 385:721–725, 1997.

O'Neill, et al., "Isoprinosine in the Treatment of Genital Warts", *Cancer Detection and Prevention*, 12:497–501 (1988).

Paca–Uccaralertkun, et al., "In vitro selection of DNA elements highly responsive to the human T–cell lymphotropic virus Type I transcriptional activator, tax", *Mol. Cell. Biol.* 14(1):456–62, 1994.

Pisetsky D, "The immunologic properties of DNA",*J Immunol* 156(2):421–3, 1996.

Pisetsky, D., "Immunologic consequences of nucleic acid therapy", *Antisense Research and Development*, 5(3):219–25 (1995).

Pisetsky, D., "Stimulation of in vitro proliferation of murine lymphocytes by synthetic oligodeoxynucleotides", *Molecular Biology Repairs*, 18:217–221, (1993).

Pottratz, et al., "17β–estradiol inhibits expression of human interleukin–6 promoter–reporter constructs by a receptor–dependent mechanism", *J. Clin. Invest.*, 93(3):944–50, 1994.

Quddus, J., et al., "Treating activated CD4$^+$ T cells with either of two distinct DNA methyltransferase inhibitors, 5–azacytidine or procainamide, is sufficient to cause a lupus–like disease in syngeneic mice", *J. Clin. Invest.*, 92(1):38–53 (1993).

Raz, et al., "Preferential induction of a Th$_1$ immune response and inhibition of specific IgE antibody formation by plasmid DNA immunization", *Proc Natl Acad Sci USA* 93(10):5141–5, (1996).

Ren, et al., Zhonghua Zhong Zazhi 16(4):247–50, 1995 HCAPLUS (198874) Abstract.

Richardson, et al., "Phenotypic and functional similarities between 5–azacytidine–treated T cells and a T cell subset in patients with active systemic lupus erythematosus",*Arthritis Rheum*, 35(6):647–62, 1992.

Rojanasakul, Y., "Antisense oligonucleotide therapeutics: drug delivery and targeting", *Adv. Drug. Delivery*, 18:115–131, 1996.

Roman M et al., "Immunostimulatory DNA sequences function as T helper–1–promoter aduvants", *Nat Med* 3(8):849–54, (1997).

Royall, et al., "Evaluation of 2',7'–dichlorofluorescin and dihydrohodamine 123 as fluorescent probes for intracellular H$_2$O$_2$ in cultural endothelial cells", *Arch. Biochem. Biophys.*, 302(2):348–55, 1993.

Sato, et al., "Immunostimulatory DNA sequences necessary for effective intradermal gene immunization", *Science*, 273:352–354, 1996.

Schnell et al., "Identification and characterization of a *Saccharomyces cerevisiae* gene (PARI) conferring resistance to iron chelators", *Eur. J. Biochem.*, 200:487–493.

Schwartz DA et al., "Endotoxin responsiveness and grain dust–induced inflammation in the lower respiratory tract", *Am J Physiol* 267(5 Pt 1):L609–17, 1994.

Schwartz DA et al., "The role of endotoxin in grain dust–induced lung disease", *Am J Respir Crit Care Med* 152(2):603–8, 1995.

Schwartz, et al., "CpG motifs in bacterial DNA cause inflammation in the lower respiratory tract", *J Clin Invest* 100(1):68–73, (1997).

Seed, et al., "A simple phase–extraction assay for chloramphenicol acyltransferase activity", *Gene* 67(2):271–7, 1988.

Sheng, et al., "Membrane depolarization and calcium induce c–fas transciption via phosphorylation of transcription factor CREB", *Neuron* 4(4):571–82, 1990.

Shirakawa, et al., "The inverse association between tubrculin responses adn atopic disorder", *Science* 275(5296):77–9, (1997).

Sparwasser, et al., "Macrophages sense pathogens via DNA motifs: induction of tumor necrosis factor–α–mediated shock", *Eur J Immunol* 27(7):1671–9, Jul. 1997.

Stein, et al., "Oligodeoxynucleotides as inhibitors of gene expression: A review", *Cancer Research*, 48:2659–2668, 1988.

Stull et al., "Antigene, ribozyme and aptamer nucleic acid drugs: progress and prospects", *Pharmaceutical Res.*, 12(4):465–483, 1995.

Subramanian et al., "Theoretical considerations on the "spine of hydration" in the minor groove of d(CGCGAATTCGCG)•D(GCGCTTAAGCGC):Monte Carlo computer stimulation", *Proc. Nat'l. Acad. Sci. USA*, 85(6):1836–1840, 1988.

Talmadge, et al., "Immunomodulatory effects in mice of polyinosinic–polycytidylic acid complexed with poly–L–l–ysine and carboxymethylcellose", *Cancer Res.* 45(3):1058–65, 1985.

Tanaka, et al., "An antisense oligonucleotide complementary to a sequence in Iγ2b increases γ2b germline transcripts, stimuulates B cell DNA synthesis, and inhibits immunoglobulin secretion", *J. Exp. Med.*, 175:597–607, 1992.

Thompson, et al., "Lymphokine–activated killer (LAK) cells V. 8–mercaptoguanosine as an IL–2 sparing agent in LAK generation", *J. Immunol.*, 145(10):3524–31, 1990.

Thorne PS., "Experimental grain dust atmospheres generated by wet and dry aerosolization techniques", *Am J Ind Med* 25(1):109–12, 1994.

Tokunaga T et al., "Synthetic oligonucleotides with particular base sequences from the cDNA encoding proteins of *Myobacterium bovis* BCG inducer interferons and activate natural killer cells", *Microbiol. Immunol.*, 36(1):55–66, 1992.

Tokunaga T et al., "A synthetic single–stranded Dna, poly(dG,dC), induces interferon–α/β and –γ, augments natural killer activity, and suppresses tumor growth", *Jpn J Cancer Res* 79(6):682–6, 1988.

Tonkinson, et al., "Patterns of intracellular compartmentalization, trafficking and acidification of 5'–fluorescein labeled phosphodiester and phosphorothioate oligodeoxynucleotides in HL60 cells", *Nucleic Acids Res.*, 22(20):4268–75, 1994.

Tsukada, et al., "Transcription factors NF–IL6 and CREB recognize a common essential site in the human prointerleukin 10 gene", *Mol. Cell. Biol.*, 14(11):7285–97, 1994.

Uhlmann et al., "Antisense oligonucleotides: A new therapeutic principle", *Chemical Reviews*, 90(4):543–584, 1990.

Wagner RW, "Gene inhibition using antisense oligodeoxynucleotides", *Nature*, 372:L333–335, 1994.

Wallace et al., "Oligonucleotide probes for the screening of recombinant DNA libraries", *Methods in Enzymology*, 152:432–442 (1987).

Weiss R., "Upping the antisense ante: Scientists bet on profits from reverse genetics", *Science*, 139:108–109, 1991.

Whalen R, "DNA vaccines for emerging infectious diseases: What if?", *Emerging Infectious Disease*, 2(3):168–175, 1996.

Whitley, et al., "A striking similarity in the organization of the E–selectin and beta interferon gene promoters", *Mol. Cell. Biol.*, 14(10):6464–75, 1994.

Wiltrout, et al., "Immunomodulation of natural killer activity of polyribonucleotides", *J. Biol. Res. Mod.*, 4(5):512–7, 1985.

Wu GY et al., "Receptor–mediated gene delivery and expression in vivo", *J. Biol. Chem.*, 263:14621–14624, 1988.

Wu–Pong S., "Oligonucleotides: Opportunities for drug and therapy research", *Pharmaceutical Technology*, 18:102–114, 1994.

Xie, et al., "Induction of CREB activity via the surface Ig receptor of B cells", *J. Immunol.*, 151(2):880–9, 1993.

Yamamoto et al., "Lipofection of synthetic oligodeoxyribonucleotide having a palindromic sequence of AACGTT to murine splenocytes enhances interferon production and natural killer activity", *Microbiol. Immunol.*, 38(10):831–836, 1994.

Yamamoto S et al., "DNA from bacteria, but not from vertebrates, induces interferons, activates natural killer cells and inhibits tumor growth", *Microbiol Immunol* 36(9):983–97, 1992.

Yamamoto S et al., "In vitro augmentation of natural killer cell activity and production of interferon–α/β and –γ with deoxyribonucleic acid fraction from *Mycobacterium bovis* BCG", *Jpn J Cancer Res* 79:866–73, Jul. 1988.

Yamamoto S et al., "Unique palindromic sequences in synthetic oligonucleotides are required to induce INF and augment INF–mediated natural killer activity", *J. Immunol.*, vol. 148(12):4072–4076, 1992.

Yamamoto S., "II. Mode of action of oligonucleotide fraction extracted from *mycrobacterium bovis* BCG", *Kekkaku*, 69(9):571–4 (29–32), 1994.

Yamamoto T et al., "Ability of olignucleotides with certain palindromes to induce interferon production and augme natural killer cell activity is associated with their base length", *Antisense Res. and Devel.*, 4(2):119–123, 1994.

Yamamoto T et al., "Synthetic oligonucleotides with certain palindromes stimulate interferon production of human peripheral blood lymphocytes", *Jpn. J. Cancer Res.*, 85:775–779, 1994.

Yi, Ae–Kyung et al., "Rapid immune activation by CpG motifs in bacterial DNA", *J Immunol.* 157:5394–5402, 1996.

Yi, A–K et al., "IFN–γ promotes IL–6 and IgM secretion in response to CpG motifs in bacterial DNA and oligodeoxynucleotides", *J Immunol* 156(2):558–64, 1996.

Zhao Q et al., "Stage specific oligonucleotide uptake in murine bone marrow B–cell precursors", *Blood* 84(11):3660–6, 1994.

Zhao Q et al., "Comparison of cellular binding and uptake of antisense phosphodiester, phosphorothioate, and mixed phosphorothioate and methylphosphonate oligonucleotides", *Antisense Res Dev* 3(1):53–66, Spring 1993.

*Antiviral Agents Bulletin*, 5(6):161–163), Jun. 1992.

* cited by examiner

IMMUNE STIMULATION BY PHOSPHOROTHIOATE OLIGONUCLEOTIDE ANALOGS

This application is a continuation of U.S. Ser. No. 08/712,135, filed Sep. 11, 1996, now U.S. Pat. No. 5,723,335 and U.S Ser. No. 08/217,988 filed Mar. 25, 1994, now abandoned.

FIELD OF THE INVENTION

This invention is directed towards methods for stimulating a localized immune response and for enhancing the efficacy of antiinfective and anticancer agents through local immune stimulation. This invention is further directed toward immunopotentiators comprising phosphorothioate oligonucleotide analogs which produce the desired immune stimulation.

BACKGROUND OF THE INVENTION

Developments in recombinant DNA technology and peptide synthesis have made possible the creation of a new generation of drugs. However, small peptides and other agents do not always invoke the immune response necessary for a therapeutic effect. Substances which increase cell-mediated and/or humoral response may be required in the formulation for efficacy. The potency of a variety of agents, particularly antiinfective and antitumor drugs, may be enhanced by stimulation of an immune response.

The cell-mediated immune response ("local immune response") is produced by T-cells or thymus derived lymphocytes. T-cells are able to detect the presence of invading pathogens through a recognition system referred to as the T-cell antigen receptor. Upon detection of an antigen, T-cells direct the release of multiple T-cell lymphokines including the interleukin-2 family (IL-2). IL-2 is a T-cell growth factor which promotes the production of many more T-cells sensitive to the particular antigen. This production constitutes a clone of T-cells. The sensitized T-cells attach to cells containing the antigen. T-cells carry out a variety of regulatory and defense functions and play a central role in immunologic responses. When stimulated to produce a cell-mediated immune response, some T-cells respond by acting as killer cells, killing the host's own cells when these have become infected with virus and possibly when they become cancerous and therefore foreign. Some T-cells respond by stimulating B cells while other T-cells respond by suppressing immune responses.

The antibody or humoral immune response ("systemic immune response") depends on the ability of B-cells, or bone marrow-derived lymphocytes, to recognize specific antigens. The mechanism by which B-cells recognize antigens and react to them is as follows. Each B cell has receptor sites for specific antigens on its surface. When an antigen attaches to the receptor site of a B-cell, the B-cell is stimulated to divide. The daughter cells become plasma cells which manufacture antibodies complementary to the attached antigen. Each plasma cell produces thousands of antibody molecules per minute which are released into the bloodstream. As the plasma cells die, others are produced, so that, once the body is exposed to a particular antigen, antibodies are produced against that antigen as long as the antigen is present in the body. Many B-cells appear to be regulated by the helper T-cells and suppressor T-cells. Helper T-cells appear to stimulate B-cells to produce antibodies against antigens, while suppressor T-cells inhibit antibody production by either preventing the B-cells from functioning or preventing the helper T-cells from stimulating the B-cells. Some B-cells, however, are T-cell independent and require no stimulation by the T-cells.

Immunopotentiators, such as adjuvants, are substances which are added to therapeutic or prophylactic agents, for example vaccines or antigens used for immunization, to stimulate the immune response. Adjuvants cause an accumulation of mononuclear cells, especially macrophages, at the site of injection. Macrophages involved in this first stage of the immune response take in the protein antigens and break them down into peptide fragments which are then exposed on the cell surface where they form a physical association with class II histocompatibility antigens. The T helper cells recognize only protein fragments associated with class II histocompatibility antigen, and not the free undegraded protein. Nonprotein antigens are similarly processed by macrophages or other antigen-presenting cells. The macrophages release monokines from the interleukin-1 family (IL-1) which stimulate the T helper cells to secrete IL-2. The actions of IL-1 and IL-2 result in the clonal expansion of T helper cells. The clonal expansion of T helper cells is followed by their interaction with B-cells, which in turn secrete antibody.

Administration of an adjuvant resulting in stimulation of IL-1 and other cytokines results in a complex spectrum of biological activities. In addition to being a primary immunostimulatory signal, IL-1 proteins have been linked with prostaglandin production, inflammation and induction of fever. IL-1 proteins have been shown to have multiple effects on cells involved in inflammation and wound healing and are known to stimulate proliferation of fibroblasts and attract cells involved in the inflammatory response.

Adjuvants encompass several broad classes including aluminum salts, surface-active agents, polyanions, bacterial derivatives, vehicles and slow-release materials. At present, most adjuvants have been found to stimulate macrophages at the site of action; however, certain adjuvants have been found to act as T-cell replacers enabling B-cells to respond to antigen in the absence of T-cells. An example of such an adjuvant is endotoxin, a B-cell mitogen.

Polynucleotides and other polyanions have been shown to cause release of cytokines. Also, bacterial DNA species have been reported to be mitogenic for lymphocytes in vitro. Furthermore, deoxyoligonucleotides (30–45 nucleotides in length) have been reported to induce interferons and enhance natural killer (NK) cell activity. Kuramoto et al. (1992) Jpn. J. Cancer Res. 83:1128–1131. Oligonucleotides that displayed NK-stimulating activity contained specific palindromic sequences and tended to be guanosine rich. Immune stimulation has also been reported for antisense oligomers that are complementary to the initiation sequence of HIV rev and to the mink cell focus-forming (MCF) envelope gene initiation region. Krieg et al. (1989) J. Immunol. 143:2448–2451; Branda et al. (1993) Biochemical Pharmacology 45:2037–2043. The MCF sequence is an endogenous retroviral sequence found in mice. In a study designed to determine whether expression of these endogenous viral sequences suppresses lymphocyte activation (as expressed infectious retroviral sequences can), antisense oligonucleotides and analogs complementary to the MCF env gene AUG region were used to inhibit expression of MCF mRNA. This resulted in increased lymphocyte activation. However, this was believed to be a specific effect resulting from inhibition of the target gene, rather than an effect of oligonucleotides per se. In this case both phosphodiester and phosphorothioate oligonucleotides complementary to this target had the same effect, whereas antisense oligonucleotides to other retroviral targets and phosphorothioate control oligonucleotides had no effect. Krieg et al. (1989) *J. Immunol.* 143:2448–2451; Branda et al. (1993) *Biochemical Pharmacology* 45:2037–2043. Branda et al. showed that an anti-rev phosphorothioate oligonucleotide analog is mitogenic in both mononuclear cells from murine spleens and human peripheral blood mononuclear cells. A concentration-dependent stimulation of immunoglobulin production was also observed in vitro and in vivo. This mitogenic effect was specific for B-cells. These effects on B-cells were believed to be specific to this anti-rev oligomer as oligonucleotides complementary to the gag-pol initiation site and the 3' splice site of endogenous retroviral sequences were known not to be stimulatory (Krieg et al. (1989) *J. Immunol.* 143:2448–2451) and because another phosphorothioate oligonucleotide analog of similar size, targeted to the human p53 protein, did not exhibit the same effect. The data suggested that endogenous retroviruses may suppress lymphocyte activation and that antisense oligonucleotides specific for these inhibitory retroviruses may reverse this suppression and stimulate B-lymphocytes. Though Branda et al. speculated about the possibility that the immune stimulation associated with this oligomer may be independent of its antisense activity, for example, contamination with endotoxin, no evidence for this could be found. Furthermore, the lymphocyte stimulation seen was to an extent not usually seen with exposure to double-stranded RNAs, which stimulate lymphokines. Immune stimulation was concluded not to be a general property of oligodeoxynucleotides, as they have been used by others to inhibit T-cell function. Branda et al. (1993) *Biochemical Pharmacology* 45:2037–2043.

The ability to reverse transforming growth factor-β (TGF-β)-mediated cellular immunosuppression in malignant glioma by addition of TGF-β2-specific phosphorothioate-antisense oligonucleotide analogs (TGF-β2-S-ODN's) has also been reported. Jachimaczak et al. (1993) *J. Neurosurg* 78:944–951. TGF-β, an immunosuppressive factor produced by malignant gliomas, is characterized by a wide range of immunoregulatory properties including depression of T-cell mediated tumor cytotoxicity, inhibition of IL-1- or IL-2-dependent T-cell proliferation, lymphokine-activated killer and natural killer cell activation, generation of cytotoxic macrophages and B-cell function. The oligonucleotide analogs in these experiments were used to block TGF-β protein synthesis at the translation level. In in vitro studies, preincubation of tumor cell cultures with TGF-β2-S-ODN's enhanced lymphocyte proliferation up to 2.5 fold and autologous tumor cytotoxicity up to 60%. Jachimaczak et al. suggested these observations may have implications for in vivo and in vitro activation of a cellular immune response against autologous malignant glioma cells by inhibiting TGF-β synthesis.

Thus, as illustrated by the above-described studies, antisense oligonucleotides and analogs have been used to specifically inhibit expression of genes implicated in immunosuppression, thus reversing the immunosuppressive effects.

An antisense oligonucleotide targeted to the cellular proto-oncogene c-myb has been demonstrated to block T-cell proliferation in peripheral blood mononuclear cells. Gewirtz et al. (1989) *Science* 245:180–183. Antisense oligonucleotides targeted to interleukin-2 (IL-2) have been shown to specifically inhibit T-cell functions, i.e., proliferation in response to allo-antigen or PHA and IL-2 production. Kloc et al.(1991) *FASEB J.* 5:A973.

Thus, antisense oligonucleotides have been used to specifically inhibit the expression of genes involved in T-cell proliferation, thus blocking proliferation and resulting in an immunosuppressive effect.

Phosphorothioate monomers and congeners thereof also have been demonstrated to affect humoral and cell-mediated immune responses. It was shown that mice treated with O,O,S-trimethyl phosphorothioate (OOS-TMP), a contaminant of malathion and other organophosphate pesticides, developed immunosuppression characterized by a decreased ability to make either humoral or cell-mediated immune responses to subsequent immunizations. Rodgers et al. (1987) *Toxicol. Appl. Pharmacol.* 88: 270–281. On the contrary, O,S,S-trimethylphosphorodithioate (OSS-TMP) enhanced the generation of humoral and cell-mediated immune responses in mice. Rodgers et al. (1988) *Toxicol.* 51:241–253.

Bacterial DNA and certain synthetic polynucleotides, both single- and double-stranded, can stimulate proliferation of lymphocytes in mice. One such example is AMPLIGEN® [polyI:poly($C_{12}$U), HEM Research Inc., Rockville, Md.], a double-stranded RNA (dsRNA) which acts as a lymphokine to mediate cellular immune activity. This includes killer cell modulation, macrophage modulation, B-lymphocyte modulation, tumor necrosis factor modulation, interferon modulation and modulation of interferon-induced intracellular enzymes. AMPLIGEN® has been reported to stabilize T4 cell counts in patients with AIDS-related complex and to have antineoplastic effects. AMPLIGEN® is a specific form of mismatched dsRNA which has a uridine substituted for every twelfth cytosine in the poly(C) strand. Poly(I):poly(C) without this mismatching was highly immunogenic but proved to be severely toxic and was abandoned as a clinical candidate in the 1970s. U.S. Pat. No. 5,194,245.

Certain synthetic oligonucleotides and analogs have been shown to be mitogenic in vitro. These oligonucleotides were polydeoxyguanosine, polydeoxycytosine or a mixture of the two. Phosphorothioates were found to be more active than the corresponding phosphodiesters. Pisetsky et al., (1993) *Life Sciences* 54:101–107. In addition, a 21-mer phosphorothioate oligonucleotide analog, ISIS 1082 (SEQ ID NO: 2), was also shown to stimulate proliferation and antibody production by murine B cells. This oligonucleotide is complementary to the translation initiation codon of the herpes simplex virus UL13 gene. It was concluded that the mitogenic effects of this and certain other oligonucleotides on B cells may be due to preferential uptake of phosphorothioates and other mitogenic oligonucleotides by B cells, and that the enhanced penetration promotes a high intracellular concentration of these compounds, leading to nonspecific activation.

Oligonucleotides having a sequence identical to a portion of the sense strand of the mRNA encoding the p65 subunit of NF-kB, a DNA binding protein, were found to stimulate splenic cell proliferation both in vitro and in vivo. The proliferating spleen cells were shown to be B cells. Immunoglobulin secretion and NF-kB activity in these cell lines was also increased by the sense oligonucleotide. Both phosphodiester and phosphorothioate sense oligonucleotides stimulated the splenocyte proliferation. The antisense phosphorothioate oligonucleotide complementary to the same region of p65 did not have this effect, and the stimulatory effect was abolished by mixing the sense and antisense oligonucleotides. Sense oligonucleotides having two mismatches from the target sense sequence also failed to elicit the proliferative effect. It was concluded that this was a sequence-specific effect which may involve direct binding of the sense sequence to specific proteins. McIntyre et al. (1993) *Antisense Res. and Devel.* 3:309–322.

It has now been found, surprisingly, that oligonucleotide analogs having at least one phosphorothioate bond can induce stimulation of a local immune response. This immunostimulation does not appear to be related to any antisense effect which these oligonucleotide analogs may or may not possess. These oligonucleotide analogs are useful as immunopotentiators, either alone or in combination with other therapeutic modalities, such as drugs, particularly antiinfective and anticancer drugs, and surgical procedures to increase efficacy. In addition, the antiinfective and anticancer effects already possessed by certain antisense oligonucleotide analogs are enhanced through such immune stimulation.

It has also been found that oligonucleotide analogs having at least one phosphorothioate bond can be used to induce stimulation of a systemic or humoral immune response. Thus, these oligonucleotides are also useful as immunopotentiators of an antibody response, either alone or in combination with other therapeutic modalities.

SUMMARY OF THE INVENTION

The present invention provides methods of stimulating a local immune response in selected cells or tissues by administering an oligonucleotide analog having at least one phosphorothioate bond to the cells or tissues. Phosphorothioate oligonucleotide analogs-have been shown to stimulate a local immune response in animals and humans. These methods are believed to be useful for enhancing the efficacy of a therapeutic treatment, particularly an antiinfective or anticancer treatment.

The present invention also provides oligonucleotide immunopotentiators having at least one phosphorothioate bond which are capable of eliciting a local inflammatory response. These oligonucleotide immunopotentiators may also possess a therapeutic activity, for example antisense activity. Several embodiments of these immunopotentiators are provided which have been shown to stimulate a local immune response in animals and humans.

DETAILED DESCRIPTION OF THE INVENTION

Oligonucleotides and oligonucleotide analogs have recently become accepted as therapeutic moieties in the treatment of disease states in animals and man. For example, workers in the field have now identified antisense, triplex, decoy and other oligonucleotide therapeutic compositions which are capable of modulating expression of genes implicated in viral, fungal and metabolic functions and diseases. Oligonucleotide drugs have been safely administered to humans and several clinical trials of antisense oligonucleotide analog drugs are presently underway. It is, thus, established that oligonucleotides and analogs can be useful therapeutic instrumentalities and that the same can be configured to be useful in regimes for treatment of cells, tissues and animals, especially humans.

The present invention provides a method for stimulating a local immune response in selected cells or tissues. The method comprises administering to selected cells or tissues an effective amount, preferably the amount needed to elicit a local inflammatory response, of an oligonucleotide analog having at least one phosphorothioate bond. It is preferred that selected cells or tissues be infected by a fungus bacterium or virus. In one embodiment, the cells are skin cells infected with a virus, such as Herpes Simplex Virus Type-1 (HSV-1), Herpes Simplex Virus Type-2 (HSV-2) or Human Papilloma Virus. In one embodiment, the tissues are condyloma acuminata (genital warts).

The present invention also provides a method for enhancing the efficacy of a therapeutic treatment, preferably treatment with an antiinfective or anticancer drug or a surgical treatment, by administering to cells or tissues an effective amount, preferably the amount needed to elicit a local inflammatory response, of an oligonucleotide analog having at least one phosphorothioate bond. In one embodiment, the cells are skin cells infected with a virus, such as Herpes Simplex Virus Type-1 (HSV-1), Herpes Simplex Virus Type-2 (HSV-2) or Human Papilloma Virus, and the therapeutic treatment is treatment with an antiviral drug or surgical excision. In one embodiment, the tissues are condyloma acuminata (genital warts).

The present invention employs phosphorothioate antisense oligonucleotide analogs which elicit a local inflammatory response. These oligonucleotide analogs can be used alone to stimulate a local immune response or can be administered in combination with another therapeutic modality, either a drug or a surgical procedure. These oligonucleotide analogs can modulate cytokine release in skin cells upon contacting skin cells with an effective amount of oligonucleotide analog. By an "effective amount" it is meant an amount sufficient to elicit an immune response resulting in the release of cytokines. In one embodiment of the invention, oligbnucleotide analogs are provided which have both therapeutic efficacy (through antisense or other means) and immunopotentiating activity. In one embodiment, the therapeutic activity is antisense activity against a foreign nucleic acid (bacterial, fungal, viral or oncogene-derived) in a host. Examples of several phosphorothioate oligonucleotide analog sequences useful in the present invention are provided in SEQ ID NO: 1, SEQ ID NO: 2 and SEQ ID NO: 3.

In the context of this invention, the term "immunopotentiator" refers to a material which produces non-specific immune stimulation. Immune stimulation can be assayed by measuring various immune parameters, for example antibody-forming capacity, number of lymphocyte subpopulations, mixed leukocyte response assay or lymphocyte proliferation assay. Immune stimulation may result in increased resistance to infection or resistance to tumor growth upon administration.

The term "oligonucleotide" refers to a plurality of joined nucleotide units formed from naturally-occurring bases and cyclofuranosyl groups joined by native phosphodiester. bonds.

"Oligonucleotide analog," as that term is used in connection with this invention, refers to moieties which function similarly to oligonucleotides but which have non naturally-occurring portions. Thus, oligonucleotide analogs may have altered sugar moieties or inter-sugar linkages. Exemplary among these are the phosphorothioate and other sulfur containing species which are known for use in the art. They may also comprise altered base units or other modifications consistent with the spirit of this invention. In accordance with this invention, at least one of the phosphodiester bonds of the oligonucleotide is replaced by a phosphorothioate bond. The oligonucleotide analog may have additional modifications to enhance the uptake, stability, affinity or other features of the oligonucleotide. Some examples of such modifications are modifications at the 2' position of the sugar such as 2'-O-alkyl modifications, preferably lower alkyl such as 2'-O-methyl and 2'-O-propyl. All such analogs are comprehended by this invention so long as they function effectively to produce an immune response. The oligonucleotide analogs in accordance with this invention preferably comprise from about 15 to about 50 subunits. As will be appreciated, a subunit is a base and sugar combination suitably bound to adjacent subunits through phosphodiester or other bonds.

Certain oligonucleotide analogs of this invention are designed to be specifically hybridizable with messenger RNA of a virus or oncogene, for example HSV-1, HSV-2, HPV or ras. This relationship between an oligonucleotide and its complementary RNA target is referred to as "antisense". These antisense oligonucleotide analogs, which also stimulate an immune response in keeping with the nature of the invention, thus can be said to have a "combination" or "multimodal" mechanism of action. Several embodiments of this type are phosphorothioate oligonucleotide analogs of SEQ ID NO: 1, SEQ ID NO: 2 and SEQ ID NO: 3.

"Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "substantially complementary" are terms which indicate a sufficient degree of complementarity such that stable and specific binding occurs between the target and the oligonucleotide or analog. It is understood that an oligonucleotide need not be 100% complementary to its target nucleic acid sequence to be specifically hybridizable. An oligonucleotide is specifically hybridizable when binding of the oligonucleotide to the target interferes with the normal function of the messenger RNA to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

The functions of messenger RNA to be interfered with include all vital functions such as translocation of the RNA to the site for protein translation, actual translation of protein from the RNA, maturation of the RNA and possibly even independent catalytic activity which may be engaged in by the RNA. The overall effect of such interference with the RNA function is to cause interference with expression of the targeted nucleic acid.

The oligonucleotide analogs of this invention are used as immunopotentiators. For therapeutic or prophylactic treatment, oligonucleotide analogs are administered to animals, especially humans, in accordance with this invention. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotides.

The pharmaceutical composition may be administered in a number of ways depending on whether local or systemic treatment is desired, and on the area to be treated. Administration may be done topically (including ophthalmically, vaginally, rectally, intranasally), intralesionally, orally, by inhalation, or parenterally, for example by intravenous drip or subcutaneous, intraperitoneal, intradermal or intramuscular injection. It is generally preferred to apply the oligonucleotide analogs in accordance with this invention topically, intralesionally or parenterally. Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

In certain embodiments, the oligonucleotide analog is administered in conjunction with a therapeutic agent, for example an antiinfective or anticancer drug, or a surgical procedure. When oligonucleotide analog is administered in conjunction with another such therapeutic modality, the oligonucleotide analog may be administered before, after and/or simultaneously with the alternative treatment. In one embodiment of the invention, the oligonucleotide analog is administered by intradermal injection to the wound area upon excision of genital warts. In another embodiment of the invention, the oligonucleotide analog is administered by intradermal injection into genital warts.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

In accordance with certain embodiments of the invention, a number of antisense oligonucleotides which are targeted to selected mRNAs were made. Natural oligonucleotides containing a phosphodiester backbone were screened for antiviral activity in an infectious yield assay. The sequences showing the best activity in this assay were synthesized as phosphorothioate analogs, the phosphorothioate backbone modification greatly enhancing the antiviral activity of the oligonucleotides through stimulation of a local immune response.

Phosphorothioate oligonucleotide analogs include at least one modified or unnatural internucleotide linkage which, in addition to its enhancement of immune stimulation, can confer stability and enhance uptake of oligonucleotide into cells. An O (oxygen) of the phosphate diester group linking nucleotides is modified to S (sulfur). Phosphorothioates often have in vivo half-lives over 24 hours and have been shown to be stable in cells, tissues, and drug formulations. Phosphorothioate oligonucleotide analogs are believed to enter cells by receptor-mediated endocytosis, and cellular uptake is often dependent on length and size, specific sequences, protein binding, and pendant modifications. Liposomes and cationic lipids can significantly enhance the uptake and fate of oligonucleotides and analogs.

ISIS 1082 (SEQ ID NO: 2), a phosphorothioate oligonucleotide analog 21 nucleotides in length targeted to the translation initiation codon for the UL13 gene of Herpes Simplex Virus (HSV) type 1 and 2, has been shown to inhibit HSV-1 replication in vitro. Synthesis of the UL13 protein in vitro by translational arrest with an $IC_{50}$ of 200–400 nm has been observed. In vitro assessment of the cellular toxicity of ISIS 1082 demonstrated that the predicted therapeutic index for the compound is equivalent to or better than that predicted for ACV in parallel assays. The demonstration that ISIS 1082 shows antiviral activity in ACV-resistant strains of virus and the favorable therapeutic index observed with the compound underscore the potential clinical value of this class of antiviral compounds. Studies have shown that the compound is minimally toxic at therapeutically relevant concentrations in vitro. The safety profile of this and other related phosphorothioates has also been evaluated in animal models. It has been observed that the compound causes an immune cell activation in rodents at the site of injection. Specifically, repeated intradermal administrations to rats elicited an infiltrate of mononuclear cells. This was believed to be a consequence of the interaction between the oligonucleotide analog and keratinocytes of the skin, and the resulting release of cytokines.

To better understand the mechanism of the local immunostimulatory response, the effects of ISIS 1082 on IL-1α release and viability in a 3-dimensional in vitro human skin model consisting of neonatal keratinocytes and fibroblasts were examined. This system was chosen because epidermal cytokines play an important role in mediating inflammatory and immune responses in the skin. Keratinocytes are the principal source of cytokines in the epidermis. This in vitro skin model displays many of the functional and metabolic properties of a differentiated epidermis and has been induced to specifically release IL-1α in response to a mixture of lipopolysaccharide/phorbol myristate acetate. Incubation of the skin model with ISIS 1082 resulted in a concentration dependent increase of cytokine release with essentially no effect on cellular viability, as measured by the Neutral Red assay. These data indicate that IL-1α, and possibly other cytokines, are released from keratinocytes in response to ISIS 1082 (SEQ ID NO: 2) may contribute to the immune cell responses seen in vivo. It was subsequently determined that an oligonucleotide (ISIS 1049, SEQ ID NO: 2) having the same sequence as ISIS 1082 but with a phosphodiester backbone did not induce IL-1α release in the skin model. To further elucidate the relationship between oligonucleotide structure and IL-1α release, a series of oligonucleotides and analogs having SEQ ID NO: 2 and either phosphorothioate (P=S) or phosphodiester (P=O) backbones were prepared. These oligonucleotide analogs were further modified at the 2' position. Table 1 shows these oligonucleotides and their ability to induce IL-1α induction from the skin model.

TABLE 1

Oligonucleotide induction of IL-1α
(all are SEQ ID NO: 2)

| ISIS # | Backbone | 2' group | Induce IL-1α? |
|---|---|---|---|
| ISIS 1049 | P = O | deoxy | no |
| ISIS 1082 | P = S | deoxy | yes |
| ISIS 7374 | P = O | C-methyl | no |
| ISIS 2007 | P = S | O-methyl | yes |
| ISIS 7389 | P = O | O-propyl | no |
| ISIS 7337 | P = S | O-propyl | yes |

The ability to induce IL-1α in this assay is correlated with the presence of the phosphorothioate backbone. It is likely that a uniformly phosphorothioate backbone is not necessary for cytokine induction, i.e., gapped, alternating or otherwise mixed backbones containing at least one phosphorothioate linkage may also induce IL-1α. These results also demonstrate that other modifications, such as the sugar modifications in this example, can also be present as long as at least one phosphorothioate is present.

Antisense oligonucleotides and analogs have been used to inhibit the replication of virus in cell culture. Studies have also shown the effectiveness of antisense oligonucleotides in animal models of viral infection. Animal models of HSV-induced keratitis are well suited for such studies. Such ocular HSV infections are usually treated topically and thus provide a relatively simple way to test the effectiveness of antisense oligonucleotides in vivo. The drugs can be applied topically in aqueous solution and several parameters of the infection can be monitored. In one experiment using a murine model, the effectiveness of the phosphorothioate antisense oligonucleotide analog ISIS 1082 (SEQ ID NO: 2) made in accordance with the teachings of the invention was tested for treatment of herpetic keratitis. It was found that topical treatment with this anti-UL13 oligonucleotide analog significantly reduced the severity of HSV-induced stromal keratitis.

Three different concentrations of the oligonucleotide analog as well as a buffer control (50 mM sodium acetate, pH 5.8, 0.15 M NaCl) and untreated animals infected with HSV-1 were tested. All animals were infected with 1×10$^5$ plaque forming units (pfu) following scratching of the cornea. It was found that treatment with 0.3% and 1.0% ISIS 1082 did not affect the severity of blepharitis, but treated mice healed slightly faster. Treatment with ISIS 1082 reduced stromal disease and vascularization on days 11, 13, and 15 post-infection. This reduction in disease was statistically significant on some days but not on others, probably because of small sample size and variability in the disease. These results indicate that antisense oligonucleotide analogs of the invention may be useful in treating HSV keratitis.

ISIS 2105 (SEQ ID NO: 1) is a phosphorothioate 20 mer complementary to the translation initiation of both HPV types 6 and 11 mRNA encoded by the HPV E2 open-reading frame. HPV-6 and HPV-11 are associated with genital warts. ISIS 2105 has been shown to inhibit E2-dependent transactivation by HPV-11 E2 expressed from a surrogate promoter. ISIS 2105 is among the first compounds to have specific antiviral effect on papillomavirus, as demonstrated by inhibition of focus formation.

The effects of ISIS 2105 on IL-1α release and viability in the 3-dimensional in vitro human skin model was examined. Incubation of the skin model with ISIS 2105 resulted in a concentration dependent increase of cytokine release similar to that seen with ISIS 1082. There was essentially no effect on cellular viability, as measured by the Neutral Red assay. These data suggest that IL-1α (and possibly other cytokines) is released from keratinocytes in response to ISIS 2105 (SEQ ID NO: 1).

Intradermal administration of ISIS 2105 in rabbits has resulted in no local or systemic toxicity. Phosphorothioate oligonucleotide analogs, both as single doses and as daily doses over a several-week period, can be administered to mice, rats and rabbits without significant acute or subacute toxicity. ISIS 2105 has also been administered to cynomolgus monkeys by intradermal injection at doses up to 10 mg/kg every other day for four weeks, and was found to be well tolerated. No antibodies to ISIS 2105 were detectable in monkey plasma at the end of the study, indicating that ISIS 2105 is not intrinsically antigenic, i.e., while it stimulates an immune response, it is not itself an antigen.

Intradermal administration of ISIS 2105 does produce a local inflammatory response, however, in all species examined, including rats, mice, rabbits, guinea pigs, monkeys and humans. This response appears to be a class effect of all phosphbrothioate oligonucleotide analogs, as similar responses were produced in rat skin by both ISIS 2105 and ISIS 1082 in 14-day studies. This response is not a delayed-type hypersensitivity involving memory T-lymphocytes but rather a result of the immunostimulation caused by these oligonucleotide analogs acting as adjuvants or immunopotentiators. Thus, while the phosphorothioate oligonucleotide analogs do not appear to be intrinsically antigenic, they are immunostimulatory. Immune stimulation is also indicated by an increased humoral immune response in rats and B-cell proliferation in the spleens of mice. Lymphoid hyperplasia in the spleen of both rats and mice, and in the lymph nodes of mice, was seen after ISIS 2105 treatment.

Mice and rats given repeated intradermal injections of ISIS 1082 (SEQ ID NO: 2) or repeated intravenous or subcutaneous injections of several other phosphorothioate oligonucleotide analogs [ISIS 2105 (SEQ ID NO: 1), ISIS 2503 (SEQ ID NO: 3, targeted to the ras oncogene)] developed, on a subacute basis, splenomegaly characterized by lymphoid hyperplasia. Lymphoid hyperplasia was also observed in lymph nodes under many experimental conditions. In addition, a predominantly mononuclear inflammatory infiltrate has been observed in other organs/tissues following repeated parenteral administration of phosphorothioate oligonucleotide analogs. These effects were not associated with any organ damage or dysfunction, and were reversible upon cessation of oligonucleotide administration.

Studies in rats to determine the association of this hyperplasia and the humoral component of the immune response to a T-cell dependent antigen demonstrated that the IgM antibody-forming cell response to the antigen was increased by 72% in rats dosed daily with ISIS 2105 at 3.3 mg/kg/day, compared with rats dosed with vehicle only. This was considered significant.

In clinical trials, 21 human subjects completed the trial with seven different dosing regimens. All subjects showed some degree of inflammation at the injection site, the extent of which was related to size and frequency of dose. Biopsies were taken from the injection sites of two of the three men in the dosing group receiving ISIS 2105 injections in the forearm twice weekly (1.02 mg/injection at 3 sites) for three weeks. Both subjects had a dense inflammatory reaction at the injection sites. This was detected by histological examination of biopsies from injection sites. There was both. T- and B-cell involvement which is indicative of a local immunological response to ISIS 2105.

Blood samples taken from three subjects at least two months after completion of the trial showed no evidence of circulating antibodies to ISIS 2105. This indicates that, as was found in monkeys, ISIS 2105 is not intrinsically antigenic in humans.

Radiolabelled ISIS 2105 has been injected intradermally into each of four genital warts (condyloma acuminata) in five male patients. Systemic absorption of radiolabelled compound was monitored by blood sampling at intervals postinjection. Warts were removed at 1, 24, 48, 72, 96, 120 and 144 hours postinjection. After injection, ISIS 2105 was localized at the site of injection with rapid absorption (70% in 4 hours). Appreciable amounts of intact drug (4 $\mu$M) still remained in the wart tissue at 72 hours. Current estimates from in vitro studies indicate that concentrations of approximately 1 $\mu$M (and perhaps lower) are therapeutically effective. The prolonged retention time at the site of injection indicates that twice-weekly intralesional injections should be sufficient for therapeutic effect.

The invention is further illustrated by the following examples which are meant to be illustrations only and are not intended to limit the present invention to specific embodiments.

EXAMPLES

Example 1

Preparation of Oligonucleotides and Analogs

Oligonucleotides and analogs were synthesized at ISIS Pharmaceuticals on an automated DNA synthesizer using standard phosphoramidite chemistry with oxidation by iodine. β-cyanoethyldiisopropyl-phosphoramidites were purchased from Applied Biosystems (Foster City, Calif.). For phosphorothioate oligonucleotide analogs, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotide analogs were synthesized according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds. 2'-O-propyl phosphorothioate oligonucleotide analogs were prepared by slight modifications of this procedure.

Prior to use in various assays, oligonucleotides and analogs were prepared by first incubating stock solutions at 37° C. for 1 hour and diluting prewarmed drug in tissue culture medium to specified concentrations. Diluted compounds were filter sterilized by centrifugation through 0.2 $\mu$m pore size Centrex filters.

Example 2

Cell Line Maintenance

HeLa (ATCC CCL2) cells were maintained as monolayer cultures in low glucose Dulbecco's Modified Eagles Medium (DME) supplemented with 10% heat inactivated fetal bovine serum (FCS) while normal human dermal fibroblasts (NHDF) [Clonetics #CC2010] were grown in Fibroblast Basal Medium (Clonetics #CC-3130) with 0.2% FCS in a 5% $CO_2$-humidified incubator at 37° C.

Example 3

In Vitro Cellular Proliferation Assay

Asynchronous, logarithmically growing HeLa cells ($10^4$) were plated in 24 well tissue culture plates in 2.0 ml of 10% DME and allowed to attach to plate surfaces overnight. The next day, medium was aspirated and 2.0 ml of medium containing increasing concentrations of ISIS 1082 or medium alone was added to each well and placed in the incubator for 5 days. At the end of the incubation period, the cells were harvested and counted in the presence of trypan blue.

Example 4

In Vitro Skin Model

The in vitro model of skin (Full thickness model ZK1200) was obtained from Advanced Tissue Sciences (La Jolla, Calif.). Nylon mesh squares of tissue derived from neonatal keratinocytes and fibroblasts were removed from storage wells containing agarose and transferred to sterile, 24 well tissue culture plates containing low glucose DME supplemented with 10% FCS and allowed to equilibrate in a 37° C. incubator overnight. The next day, the growth medium was removed and replaced with assay medium (DME, 2% FCS) containing oligonucleotide and incubated with the tissue for 24 hours.

Example 5

Neutral Red Assay

The keratinocyte tissue substrates were incubated for 24 hours at 37° C., 5% $CO_2$, 90% humidity in the presence of oligonucleotide or LPS/PMA in assay media. The test agents were removed, replaced with neutral red solution (50 μg/ml), and incubated for 3 hours. The neutral red was removed and tissue substrates were washed with PBS. After a brief exposure to 0.5% formaldehyde/1% calcium chloride solution, incorporated dye was extracted using 1% acetic acid in 50% aqueous ethanol. The color intensity of the solution, measured at 540 nm, was proportional to viability of cells after drug exposure.

Example 6

Human IL-1α Immunoassay

A murine monoclonal antibody specific for IL-1α was applied to microtiter plates. A 200 μl aliquot of sample supernatant was pipetted into the wells and incubated at room temperature for 2 hours. After washing away any unbound proteins, a polyclonal antibody against IL-1α conjugated to horseradish peroxidase was added to the wells to sandwich any immobilized IL-1α and incubated for 1 hour at room temperature. Following a wash to remove any unbound antibody-enzyme, a substrate solution of hydrogen peroxide and tetramethylbenzidine was added to the wells and color developed in proportion to the amount of bound IL-1α. The color development was terminated by the addition of 2N sulfuric acid and the intensity of the color was measured at 450 nm.

Example 7

Immunological Evaluation of ISIS 2105 in Rats

The effects of repeated administration of ISIS 2105 to rats on the humoral component of the immune response to a T-cell dependent antigen were determined. Lymphoid hyperplasia in the spleen and lymph nodes of rats dosed with ISIS 2105 had previously been observed. Histomorphologic changes were found to be associated with increased antibody production capacity in the spleen. Doses of 0.033, 0.18, 0.33 or 3.3 mg/kg/day were administered intradermally to groups of 5 female Sprague-Dawley rats daily for 14 days. The control group was given vehicle alone. A positive control group received cyclophosphamide (25 mg/kg/day) by intraperitoneal injection on days 11–14 of the study. All animals were sensitized to sheep RBCs on day 11 by intravenous injection. At the end of the 14-day dosing period, the rats were euthanized and terminal body weights, spleen and thymus weights were recorded. The IgM antibody-forming cell response of the spleen was determined ex vivo in spleen homogenates by quantifying plaque formation after addition of sheep RBCs. High-dose animals had increased spleen weights, both absolute (55%) and percent of body weight (48%), and an increased spleen cellularity (27%) compared to vehicle-treated animals. The IgM antibody-forming cell response to the T-dependent sheep erythrocyte antigen, when evaluated as total spleen activity, was increased by 72% in the 3.3 mg/kg/day group compared to vehicle-treated animals. This was considered to be significant. The positive control, cyclophosphamide, produced anticipated decreases in immune parameters. In conclusion, ISIS 2105 appeared to enhance the humoral response in rats receiving 3.3 mg/kg/day.

Example 8

Immunological Evaluation of ISIS 2105 in Mice

The effects of ISIS 2105 on various immune parameters in female B6C3F1 mice when administered by intradermal injection daily for 14 days were determined. Lymphoid hyperplasia in the spleen of mice dosed with ISIS 2105 had previously been observed. Groups of 5 females each received doses of 0 (vehicle control), 0.066, 0.33, 0.66 or 6.6 mg/kg/day. On the day after the last injection (day 15), the animals were sacrificed, spleens were removed and weighed, and a spleen cell homogenate was prepared for determination of immunologic parameters, including enumeration of lymphocyte subpopulations using specific antibodies, the mixed leukocyte response (MLR) assay, and the lymphocyte proliferation assay. No animals died during the study, and there were no treatment-related effects on body weight or weight gain. Spleen weight (both absolute and relative to body weight) was increased by approximately 50–60% in the high-dose group (6.6 mg/kg/day) and this was associated with increases in total spleen cell number (35%) and in the fraction of Ig+ cells (45%) which is a marker for B-lymphocytes. Results at the lower doses were inconsistent. The MLR, an indicator of T-cell-dependent immune function, was decreased at the two highest doses, but there was no effect on the spleen cell proliferative response to the T-cell mitogen, Con A, at any dose level, which indicates that the proliferative capacity of T-lymphocytes was not altered. These results are somewhat inconsistent and must be considered preliminary; however, it was concluded that the high doses of ISIS 2105 may cause a form of immunostimulation.

Example 9

Intradermal Injection of ISIS 2105 in Humans

ISIS 2105 for clinical trials was formulated as sterile phosphate-buffered solution for intradermal injection of volumes of 0.1 ml to 0.15 ml per injection. The concentration of ISIS 2105 varied depending on desired dose. Intradermal injections of ISIS 2105 were given into the ventral surface of the forearm of healthy male volunteers.

Example 10

Immunostimulatory Response in Humans

Skin biopsies were performed in two human subjects following administration of 5 doses of 1.02 mg of ISIS 2105. A skin ellipse measuring 1.2×0.5 cm having a central pigmented area of 0.2 cm was removed from the forearm injection site. This ellipse was bisected and processed for microscopic histological analysis. The histological analysis revealed a moderately dense, inflammatory infiltrate in all layers of the dermis from both subjects. Immunohistochemistry revealed a mixture of cell types present. T-cells were predominant; however, B-cells were also present suggesting the immunological response was both T-cell and B-cell in nature.

Example 11

Injection of ISIS 2105 into Genital Warts in Human Subjects

To evaluate its pharmacokinetics, the phosphorothioate oligonucleotide analog ISIS 2105 (SEQ ID NO: 1) was $^{14}$C labeled in the 2-position of thymine. Approximately 1 mg (3.5 μCi/mg) was injected intradermally in each of four genital warts (condyloma acuminata) in five male patients. Systemic absorption of radiolabelled compound was monitored by blood sampling 1, 4, 8, 12, 24, 48, 72 and 144 hours postinjection. Warts were removed at 1, 24, 48, 72, 96, 120 and 144 hours postinjection. Urine and $CO_2$ samples for $^{14}C$ analysis were taken at intervals postinjection. Safety monitoring of these patients revealed no clinically significant abnormalities. After injection, ISIS 2105 was rapidly absorbed (70% in 4 hours). However, appreciable amounts of intact drug (4 $\mu$M) remained in the wart tissue at 72 hours. Current estimates indicate that concentrations of approximately 1 $\mu$M are therapeutically effective. Peak plasma concentrations were achieved within 1 hour following the absorption of labeled ISIS 2105 from the injection site. Drug was cleared from plasma with a rapid distribution and prolonged elimination phase. The total body elimination half-life was estimated at 156 hours. The oligonucleotide was slowly metabolized and the radiolabel was eliminated, principally as $CO_2$ in expired air and in urine. In summary, following a single dose, intact ISIS 2105 was localized at the site of injection with rapid absorption but prolonged retention time in wart tissue. This indicates that twice-weekly intralesional injections should be sufficient for therapeutic effect.

Example 12

Evaluation of ISIS 2105 as Surgical Adjuvant Therapy

Condyloma acuminata (genital warts) measuring at least 1×1 $mm^2$ are surgically removed. Upon cessation of bleeding with electrocautery, skin surrounding the ablated area is injected with 0.1 cc of ISIS 2105 drug formulation containing 0.3 mg or 1 mg of ISIS 2105. Up to 4 warts are treated.

What is claimed:

1. A method for treating prophylactically a human to stimulate a cell-mediated immune response comprising:

administering to the human as an immunopotentiator an amount of a phosphorothioate oligonucleotide analog effective to stimulate a cell-mediated immune response.

2. The method of claim 1, wherein the phosphorothioate oligonucleotide analog is not antisense.

3. A method for treating a human who has cancer comprising:

administering to the human as an immunopotentiator an amount of a phosphorothioate oligonucleotide analog effective to stimulate a cell-mediated immune response.

4. The method of claim 3, wherein the phosphorothioate oligonucleotide analog is not antisense.

5. A method for treating a human who has an infection comprising:

administering to the human as an immunopotentiator an amount of a phosphorothioate oligonucleotide analog effective to stimulate a cell-mediated immune response.

6. The method of claim 5, wherein the phosphorothioate oligonucleotide analog is not antisense.

7. A method for treating a human having surgery comprising:

administering to the human as an immunopotentiator in conjunction with the surgery an amount of a phosphorothioate oligonucleotide analog effective to stimulate a cell-mediated immune response.

8. The method of claim 7, wherein the phosphorothioate oligonucleotide analog is not antisense.

9. A method for treating therapeutically a human, comprising:

administering to a human subject in need of such treatment as an immunopotentiator an amount of a phosphorothioate oligonucleotide analog effective to stimulate a cell-mediated immune response, wherein the phosphorothioate oligonucleotide analog is not antisense.

10. A method of enhancing the efficacy of a therapeutic or prophylactic treatment for a human subject by stimulating a cell-mediated immune response, comprising:

administering to the human subject as an immunopotentiator in conjunction with the treatment an amount of a phosphorothioate oligonucleotide analog effective to stimulate a cell-mediated immune response.

11. The method of claim 10, wherein the phosphorothioate oligonucleotide analog is not antisense.

12. The method of claim 10, wherein the treatment is an anti-infective agent.

13. The method of claim 10, wherein the treatment is an anti-cancer agent.

14. The method of claim 10, wherein the treatment is surgery.

* * * * *

SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 1:

TTGCTTCCAT CTTCCTCGTC        20

(2) INFORMATION FOR SEQ ID NO: 2:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 2:

GCCGAGGTCC ATGTCGTACG C        21

(2) INFORMATION FOR SEQ ID NO: 3:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 3:

TCCGTCATCG CTCCTCAGGG        20